US006850465B2

(12) United States Patent
Rohwedder

(10) Patent No.: US 6,850,465 B2
(45) Date of Patent: Feb. 1, 2005

(54) PULSE GENERATING DRIVE CIRCUIT FOR AN ELECTROMAGNETIC SOURCE FOR GENERATING ACOUSTIC WAVES

(75) Inventor: Arnim Rohwedder, Fuerth (DE)

(73) Assignee: Siemens Aktiengesellschaft, Münich (DE)

( * ) Notice: Subject to any disclaimer, the term of this patent is extended or adjusted under 35 U.S.C. 154(b) by 0 days.

(21) Appl. No.: 10/342,016

(22) Filed: Jan. 14, 2003

(65) Prior Publication Data

US 2003/0161217 A1 Aug. 28, 2003

(30) Foreign Application Priority Data

Feb. 22, 2002 (DE) ........................................ 102 07 737

(51) Int. Cl.[7] .............................. H04R 1/02; A61B 8/00

(52) U.S. Cl. ....................................... 367/137; 600/439

(58) Field of Search ................................. 367/137, 138, 367/175; 331/166; 327/110, 111; 600/439; 601/4

(56) References Cited

U.S. PATENT DOCUMENTS

| | | | | |
|---|---|---|---|---|
| 3,916,373 A | * | 10/1975 | Schroder | 367/137 |
| 4,674,505 A | | 6/1987 | Pauli et al. | |
| 4,736,130 A | * | 4/1988 | Puskas | 310/316.01 |
| 5,251,630 A | | 10/1993 | Rattner | |
| 6,121,732 A | * | 9/2000 | Parker et al. | 315/209 R |

* cited by examiner

*Primary Examiner*—Ian J. Lobo
(74) *Attorney, Agent, or Firm*—Schiff Hardin LLP

(57) ABSTRACT

A circuit for driving an electromagnetic source for generating acoustic waves has a dischargeable high-voltage capacitor with a diode or a diode module connected in parallel therewith.

7 Claims, 4 Drawing Sheets

PULSE GENERATING DRIVE CIRCUIT FOR AN ELECTROMAGNETIC SOURCE FOR GENERATING ACOUSTIC WAVES

BACKGROUND OF THE INVENTION

1. Field of the Invention

The present invention is directed to a drive circuit which generates a pulse for an electromagnetic source for generating shockwaves of the type including a dischargeable high-voltage capacitor.

2. Description of the Prior Art

A known circuit of the above type is shown in FIG. 1. The circuit has a constant voltage source 1, a switch 2, which is usually implemented as a spark gap, a high-voltage capacitor 3 as well as a coil, which is part of an acoustic wave-generating unit of an electromagnetic shockwave source. In addition to the coil 4, the acoustic wave-generating unit of the electromagnetic source has a coil carrier (not shown) on which the coil 4 is arranged and a magnetically susceptible membrane (likewise not shown) arranged on the coil 4 with an intervening insulator. Upon discharge of the high-voltage capacitor 3 across the coil 4, a current I flows through the coil 4, and the resulting electromagnetic field interacts with the membrane. The membrane is thereby repelled into an acoustic propagation medium, as causing pressure waves to be emitted into the acoustic propagation medium as a carrier medium between the acoustic wave-generating unit of the electromagnetic source and a subject to be acoustically irradiated. Shockwaves can arise from the acoustic source pressure waves due to non-linear effects in the carrier medium. The structure of such an electromagnetic shockwave source is disclosed in European Application 0 133 665 as an example.

When the circuit shown in FIG. 1 is operated for generating acoustic waves, then the curves of the voltage U, of the current I and of the square of the current I ($I^2$) shown as examples in FIG. 2 occur during the discharge event of the high-voltage capacitor 3 across the coil 4, upon the circuit being shorted by means of the switch 2. Curve 5 shows the voltage curve across the coil 4, and curve 6 shows the decaying current I flowing through the coil 4, this current I, as already mentioned, being the cause for generating acoustic waves. Curve 7 illustrates the square of the current I.

The acoustic waves generated by the electromagnetic shockwave source are proportional to the square of the current I. As can be seen from FIG. 2 on the basis of the square of the current I, a first acoustic source pressure wave from the first acoustic pressure pulse (1st maximum) and further acoustic source pressure waves from the decaying sequence of positive acoustic source pressure pulses, proceed from a discharge event of the high-voltage capacitor 3. Due to non-linear effects in the carrier medium and a non-linear focusing, which usually ensues with a known acoustic focusing lens, the first source pressure wave and the following source pressure waves can form into shockwaves with short, intensified positive components and subsequent, elongated, under-pressure troughs, as already mentioned.

Shockwaves are utilized, for example, for non-invasive disintegration of calculi from the onside of the body of a patient, for example for destroying a kidney stone. The result of the shockwaves directed onto the kidney stone is that cracks arise in the kidney stone. The kidney stone ultimately breaks apart and thus can be eliminated in a natural way.

The first shockwave that proceeds from the first source pressure pulse is the determining factor for the concretiondisintegrating growth of cracks in the stone. Due to the greatly increased proliferation rate caused by the under-pressure trough of the first shockwave, the following shockwaves lead to only superficially acting cavitation processes that can even be harmful to tissue.

SUMMARY OF THE INVENTION

An object of the present invention is therefore based on the object of fashioning a circuit of the species initially cited such that the generation of acoustic waves is improved.

This object is inventively achieved in a circuit for driving an electromagnetic source for generating acoustic waves, having a dischargeable high-voltage source across which a diode branch (diode or a diode module) is connected in parallel, with the polarity of the charging voltage for the high-voltage capacitor and the polarity of the diode branch being set so, that the diode branch is non-conducting for current produced by the charging voltage. The diode module can be formed of series circuits and/or parallel circuits of diodes. A temporal lengthening of the first source pressure pulse in the discharge of the high-voltage capacitor is achieved by connecting the diode or the diode module in parallel with the high-voltage capacitor. Moreover, the subsequent, decaying source pressure pulse is highly attenuated dependent on the diode impedance or impedances. The attenuation can be so large that the subsequent source pressure pulse even disappears entirely. Due to the temporal lengthening of the first source pressure pulse, a stronger first acoustic wave in, for example, the generation of shockwaves, i.e. a stronger first shockwave, is generated, resulting in an intensification of the disintegrating effect for the disintegration of calculi. The tissue-damaging cavitation caused by shockwaves that follow the first shockwave and have proceeded from the following source pressure pulses also are diminished, with only very few weak source pressure pulses or no source pressure pulses following the first source pressure pulse arise. Moreover, the service life of the high-voltage capacitor is lengthened due to the reduced repolarization voltage caused by the diode or the diode module. Given the generation of shockwaves from the acoustic waves, moreover, less audible shockwaves are generated, so that a reduction of the noise occurs. A determining factor in the generation of audible acoustic waves when generating shockwaves is the total area under the curve of the square of the current, i.e. the integral of the square of the current over the time. In the case of the present invention, this is reduced overall by the elimination of the source pressure pulses that normally follow the first source pressure pulse.

In one version of the invention, the circuit has a switch formed by one or more thyristors, preferably series-connected thyristors, with a high-current diode with a slow release time or a diode module formed by at least two high-current diodes with slow release time, connected in parallel with the high-voltage capacitor. According to one version of the invention, the diode module is a series circuit of high-current diodes with slow release time.

As used herein, high-current diodes with slow release time means known power diodes with a release time or storage time lies in the $\mu$s range. In contrast thereto, small-signal diodes exhibit release times of advantageously 10 through 100 ns, and very fast diodes such as FRED or Schottky diodes exhibit release times on the order of magnitude of 100 ps.

DESCRIPTION OF THE PREFERRED EMBODIMENTS

Figure 3:
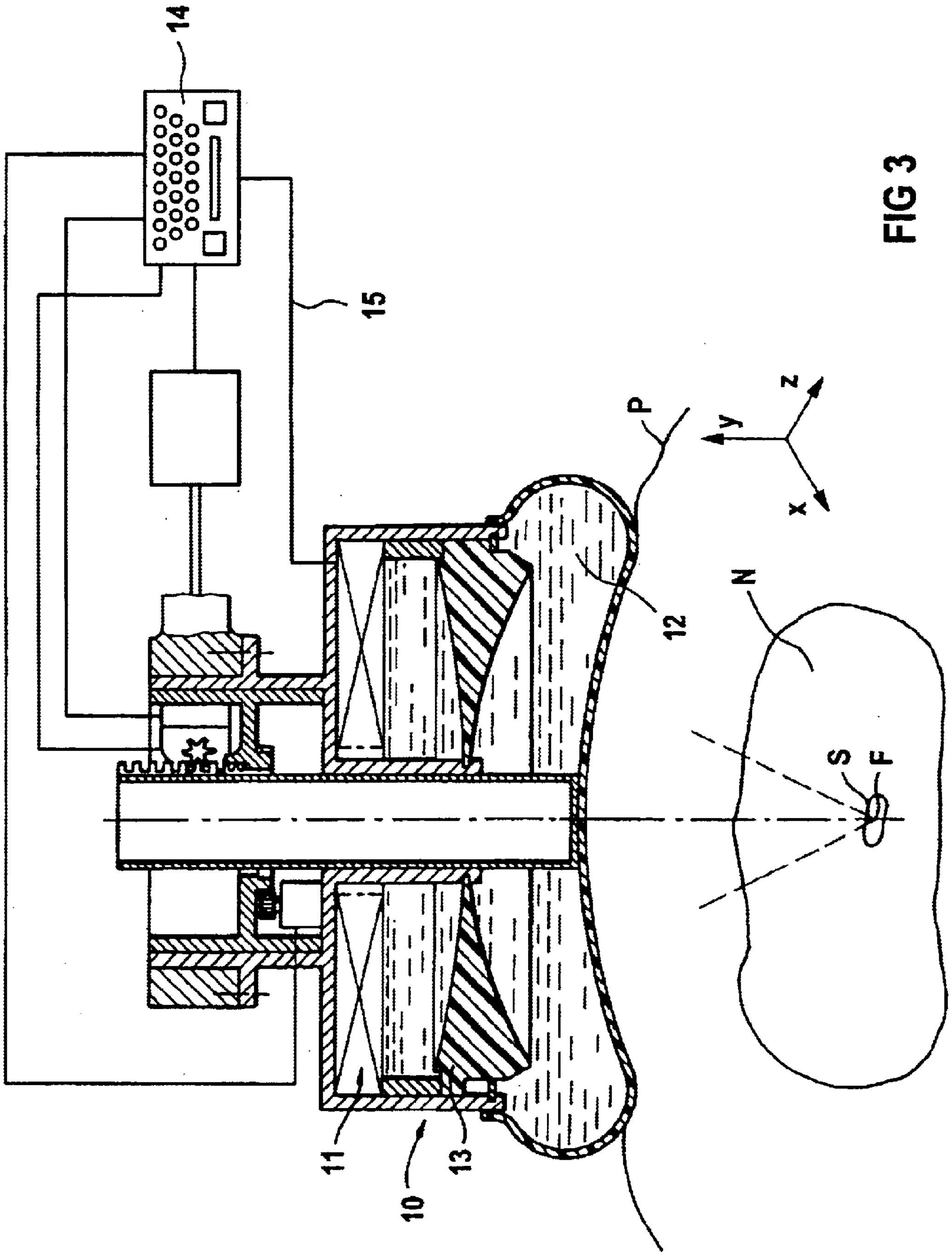
FIG. 3 is a schematic illustration, partly in section of an electromagnetic shockwave source operable with the inventive circuit.

In an illustration partially as a sectional view and partially as a block diagram, FIG. 3 shows an electromagnetic shockwave source in the form of a therapy head 10 that is a component of a lithotripsy apparatus (not shown in detail) in the exemplary embodiment. The therapy head 10 has a known acoustic wave-generating unit 11 that operates according to the electromagnetic principle. In a way that is not shown in FIG. 3, the acoustic wave-generating unit 11 has a coil carrier, a flat coil arranged thereon, and a metallic membrane that is insulated from the flat coil. For generating shockwaves, the membrane—as a result of electromagnetic interaction with the coil—is repelled into an acoustic propagation medium 12, causing a source pressure wave to be transmitted into the acoustic propagation medium 12. The source pressure wave is focused onto a focus zone by an acoustic lens 13, causing the source pressure wave to intensify to a shockwave during its propagation in the acoustic propagation medium and after introduction into the body of a patient P. In the exemplary embodiment shown in FIG. 3, the shockwave serves the purpose of disintegrating a stone S in the kidney N of the patient P.

Figure 4:
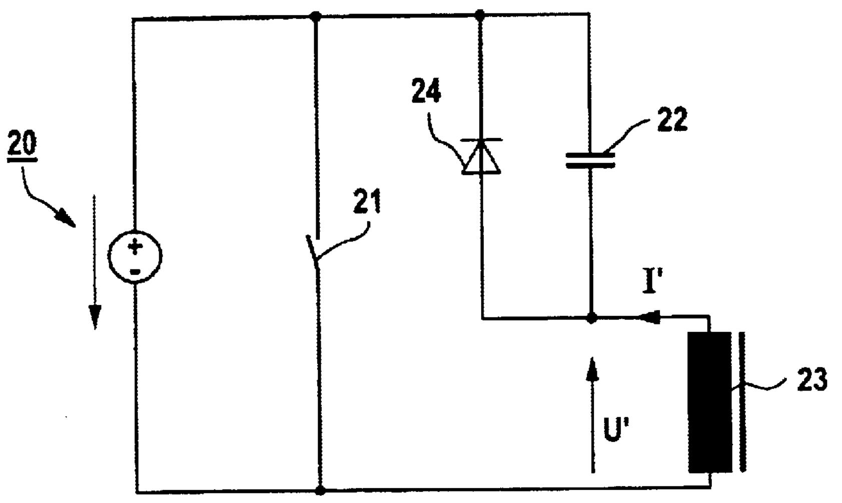
FIG. 4 shows an inventive circuit for driving an electromagnetic source for generating acoustic waves.

The therapy head 10 has an operating and supply unit 14 allocated to it that, except for the flat coil, includes the inventive circuit for generating acoustic waves that is shown in FIG. 4. The operating and supply unit 14 is electrically connected to the acoustic wave-generating unit 11 controlling the flat coil via a connecting line 15 shown in FIG. 3.

Figure 1:
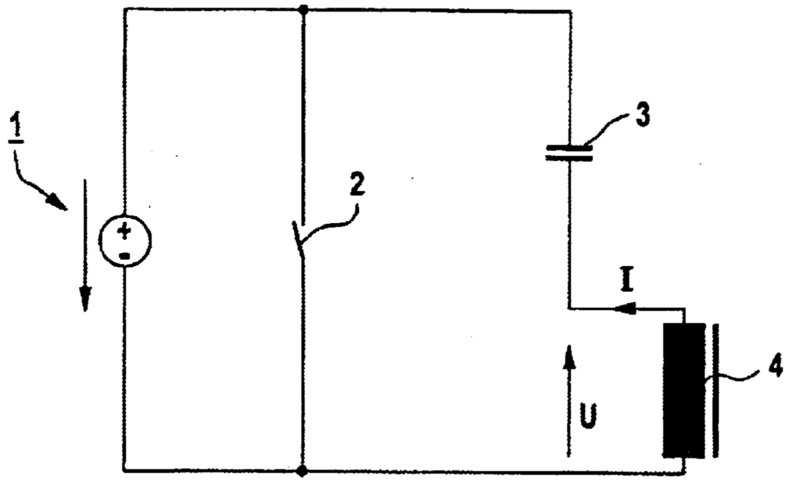
FIG 1 (PRIOR ART)
FIG. 1, as described above, is a known circuit for driving an electromagnetic source for generating acoustic waves.
Figure 2:
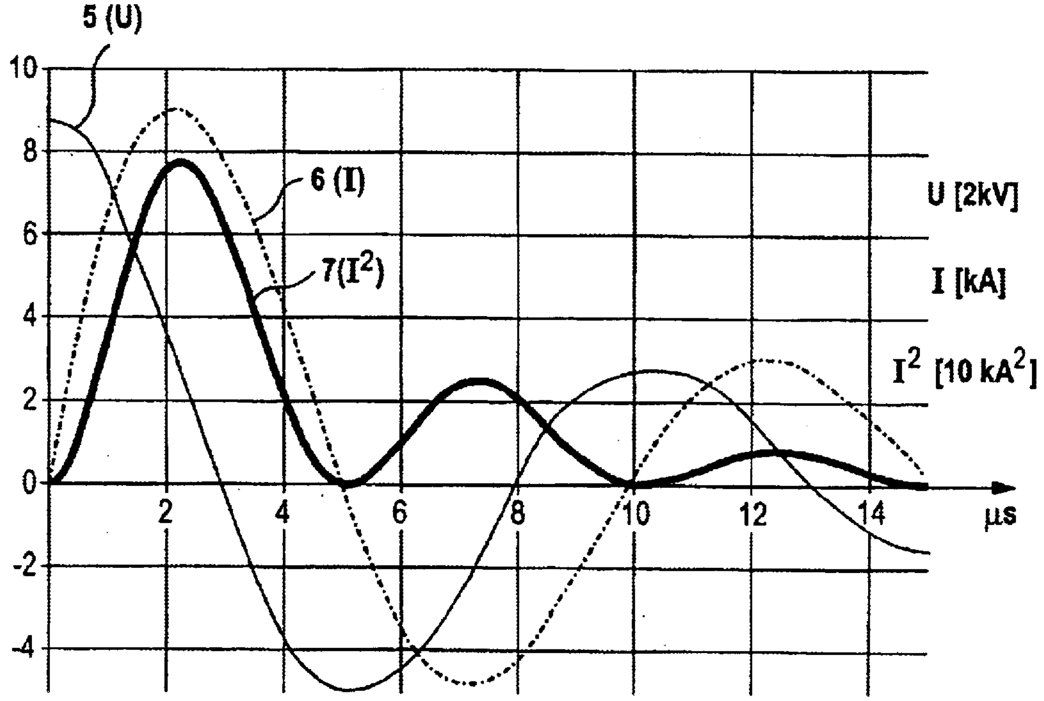
FIG 2 (PRIOR ART)
FIG. 2, as described above, shows the curve of the voltage U, the current I and the square of the current I over the time during the discharge of the high-voltage capacitor of the circuit of FIG. 1.
Figure 5:
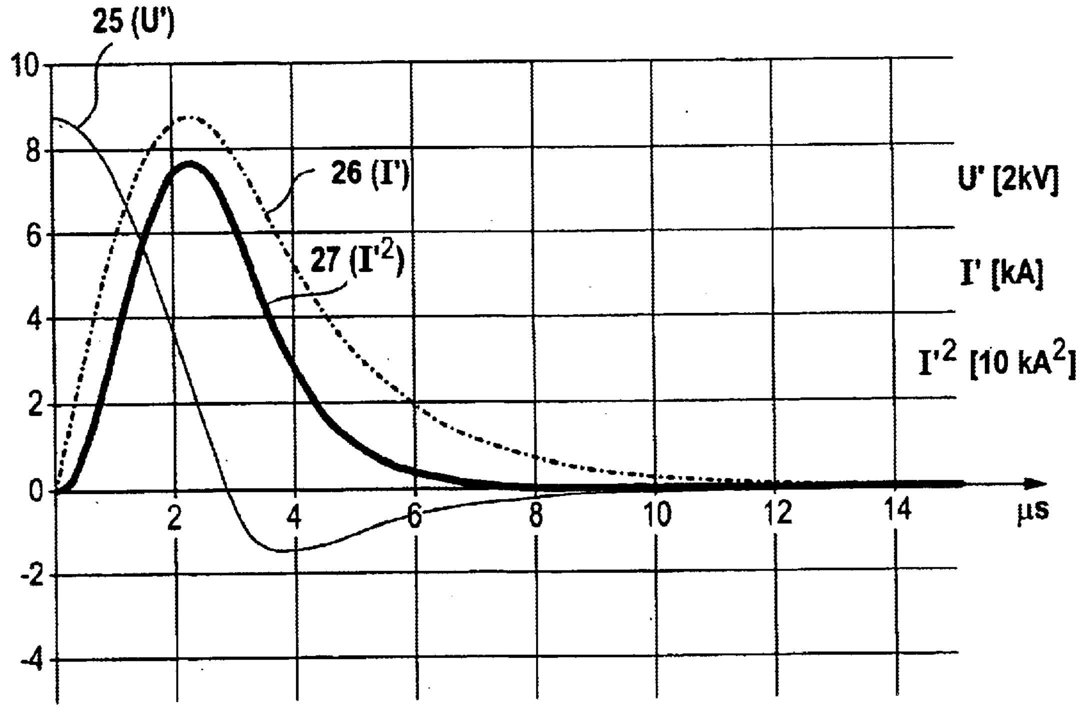
FIG. 5 shows the curves of the voltage U', of the current I' and the square of the current I' over the time during the discharge of the high-voltage capacitor of the circuit of FIG. 4.

The circuit shown in FIG. 4 for an electromagnetic shockwave source for generating acoustic waves has a constant voltage source 20, a switch 21, a high-voltage capacitor 22 and the flat coil 23 of the electromagnetic acoustic wave-generating unit 11 of the therapy head 10. Moreover, a diode 24 is inventively connected in parallel directly across the high-voltage capacitor 22. The diode 24 is connected in the non-conducting direction relative to the polarity of the charging voltage of the high-voltage capacitor 22. The advantages of this inventive circuit for the discharge of the high-voltage capacitor 22 for generating shockwaves are explained with reference to FIG. 5, which shows the curve 25 of the voltage U', the curve 26 of the current I' and the curve 27 of the square of the current I'. The circuits shown in FIGS. 1 and 4 were operated under the same boundary conditions for producing the respective set of curves shown in FIGS. 2 and 5. As can be derived from FIG. 5 in comparison to FIG. 2, the curve of the square of the current I'' now has only one maximum and then continuously decays over time, and the area under the square of the current I' has simultaneously increased compared to the area under the first maximum of the square of the current I from FIG. 2. Since an acoustic source pressure wave generated with the sound-generating unit 11 is proportional to the square of the current I', it is clear from FIG. 5 that an intensified first shockwave is produced by the circuit shown in FIG. 4, resulting in an intensification of the volume disintegration, i.e. an improved effect for the destruction of the stone S of the kidney N derives. Since, additionally, the curve 27 of the square of the current I' exhibits no further maximums, this means that no further source pressure waves that intensify into shockwaves arise beyond the first source pressure wave. Therefore, tissue-damaging cavitations due to the shockwaves following the first shockwave in the known generation of shockwaves do not occur in the inventive generation of a shockwave. Further, the service life of the high-voltage capacitor 22 is extended due to a reduced repolarization voltage of the high-voltage capacitor 22 that is created by the diode 24. A further advantage is the reduction of the generation of audible sound waves in the generation of shockwaves, since the overall area under the curve 27 of the square of the current I', which is the determining factor for the generation of audible acoustic waves in the generation of shockwaves, is reduced compared to the overall area under the curve 7 of the square of the current.

Figure 6:
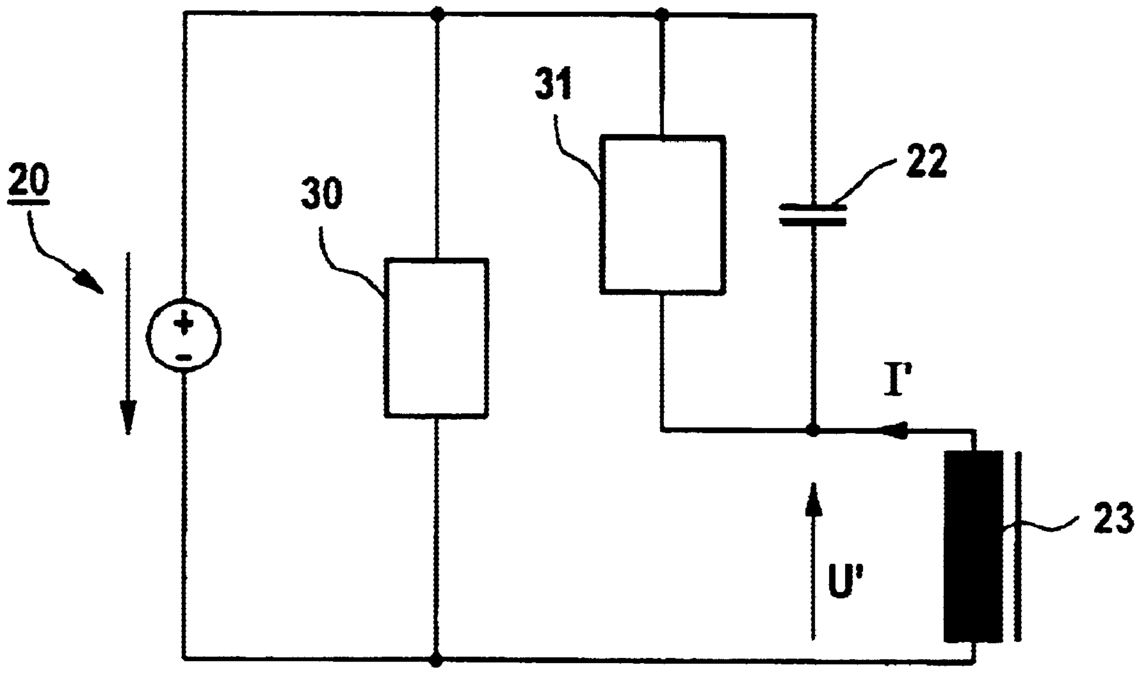
FIG. 6 shows another version of the inventive circuit with a series circuit of thyristors as a switch means.

FIG. 6 shows a second inventive circuit for an electromagnetic shockwave source that differs from the circuit shown in FIG. 4 by the use, as schematically indicated, of a series circuit of known thyristors as a switch means 30, and, as is likewise schematically shown the use of a diode module 31 formed by a series circuit of high-current diodes with slow release time connected directly in parallel with the high-voltage capacitor 22. The circuit shown in FIG. 6 works essentially the same as the circuit shown in FIG. 4 and likewise leads to the advantages of the invention that were already explained for the circuit of FIG. 4 on the basis of FIG. 5.

Although modifications and changes may be suggested by those skilled in the art, it is the intention of the inventor to embody within the patent warranted hereon all changes and modifications as reasonably and properly come within the scope of his contribution to the art.

I claim as my invention:

1. An electromagnetic source for generating acoustic waves for vivo disintegration of calculi, comprising:

a coil and a magnetically susceptible membrane disposed next to said coil with an intervening insulator and;

a drive circuit connected to said coil comprising, a dischargeable high-voltage capacitor connected in series with said coil, a diode branch connected in parallel with said capacitor, and said capacitor, when discharged, causing said membrane to be repelled from said coil to generate a pressure pulse sequence that produces said acoustic waves, with said diode branch causing a first pressure pulse in said sequence to be temporally lengthened and subsequent pressure pulses in said sequence to be attenuated.

2. An electromagnet source as claimed in claim 1 wherein said diode branch consists of a single diode.

3. An electromagnet source as claimed in claim 1 wherein said diode branch comprises a diode module.

4. An electromagnet source as claimed in claim 3 wherein said diode module comprises a plurality of diodes connected in series.

5. An electromagnet source as claimed in claim 3 wherein said diode module comprises a plurality of diodes connected in parallel.

6. An electromagnet source as claimed in claim 1 further comprising a switch connected across said capacitor and said diode branch, and said coil, formed by at least one thyristor, and wherein said diode branch comprises at least one high-current diode having a slow release time.

7. An electromagnet source as claimed in claim 6 wherein said diode branch comprises a plurality of high-current diodes with slow release time connected in series.

* * * * *